United States Patent [19]

Berner et al.

[11] Patent Number: 5,064,654
[45] Date of Patent: Nov. 12, 1991

[54] MIXED SOLVENT MUTUALLY ENHANCED TRANSDERMAL THERAPEUTIC SYSTEM

[75] Inventors: Bret Berner, Scarsdale, N.Y.; Charles Ebert, Salt Lake City, Utah; Gerard C. Mazzenga, New City; John H. Otte, Monsey, both of N.Y.

[73] Assignee: Ciba-Geigy Corporation, Ardsley, N.Y.

[21] Appl. No.: 512,639

[22] Filed: Apr. 20, 1990

Related U.S. Application Data

[63] Continuation of Ser. No. 296,910, Jan. 11, 1989, abandoned, which is a continuation of Ser. No. 133,681, Dec. 16, 1987, abandoned.

[51] Int. Cl.$^5$ .............................................. A61F 13/02
[52] U.S. Cl. .................................... 424/448; 424/449
[58] Field of Search ............... 424/443, 447, 448, 449; 604/304, 897

[56] References Cited

U.S. PATENT DOCUMENTS

| | | | |
|---|---|---|---|
| 4,379,454 | 4/1983 | Campbell et al. | 424/448 |
| 4,460,372 | 7/1984 | Campbell et al. | 604/897 |
| 4,588,580 | 5/1986 | Gale et al. | 604/304 |
| 4,675,009 | 6/1987 | Hymes et al. | 604/304 |
| 4,681,584 | 7/1987 | Gale et al. | 424/449 |

FOREIGN PATENT DOCUMENTS

| | | |
|---|---|---|
| 43738 | 1/1982 | European Pat. Off. . |
| 129284 | 12/1984 | European Pat. Off. . |
| 216822 | 12/1984 | Japan . |
| 152281 | 8/1985 | Japan . |
| 155113 | 8/1985 | Japan . |
| 40214 | 2/1986 | Japan . |
| 2093694 | 9/1982 | United Kingdom . |

OTHER PUBLICATIONS

Chaudry et al., 13th International Symposium on Controlled Release of Bioactive Materials (1986) pp. 136–137.
Scheuplin et al., Physiological Review, vol. 51, No. 4, pp. 702–747 (1971).
Guy et al., International Journal of Pharmaceutics, vol. 32, pp. 159–163 (1986).
Cooper et al., The Transdermal Delivery of Drugs, vol. II ed., pp. 57–62 (1986).
Rohr et al., Abstracts, 39th National Meeting, vol. 15, No. 3, p. 75 (1985).
Ghanem et al., Pharmaceutical Res., vol. 3, No. 5, p. 56S (Oct. Supplement).
Good et al., Journal of Controlled Release, vol. 2, pp. 89–97 (1985).
Jimbo et al., The Journal of Dermatology, vol. 10, pp. 241–250 (1983).
Roberts et al., J. Pharm. Pharmac., vol. 27, pp. 599–605 (1975).
Drug Development and Industrial Pharmacy, vol. 12, pp. 465–469 (1986).
Schulze, Fette Seifen Anstrichmittel, vol. 73, No. 5, pp. 319–324 (1971).
Scheuplein et al., The Journal of Investigative Dermatology, vol. 60, No. 5, pp. 286–296 (1973).
Chem. Pharm. Bull., vol. 35, No. 7, pp. 3054–3057 (1987).
Ghanem et al., Journal of Controlled Release, vol. 6, pp. 75–83 (1987).
De Noble et al., Pharmaceutical Research, vol. 4, No. 2, p. 59 (1987).
International Journal of Pharmaceutics, vol. 33, pp. 37–43 (1986).
Nagai et al., Journal of Controlled Release, vol. 1, pp. 239–246 (1985).
Inagi et al., Chem. Pharm. Bull., vol. 29, No. 6, pp. 1708–1714 (1981).

Primary Examiner—Thurman K. Page
Assistant Examiner—D. Gabrielle Phelan
Attorney, Agent, or Firm—JoAnn Villamizar

[57] ABSTRACT

The invention relates to the art of transdermal administration of drug substances, particularly those drug substances having a greater solubility in ethanol than in water and those drug substances having cationic or anionic substituent groups. It is especially useful for the administration of nitroglycerin.

11 Claims, 6 Drawing Sheets

MIXED SOLVENT MUTUALLY ENHANCED TRANSDERMAL THERAPEUTIC SYSTEM

This application is a continuation, of application Ser. No. 296,910, filed Jan. 11, 1989 now abandoned, which is a continuation, of application Ser. No. 133,681, filed 12/16/87, abandoned.

BACKGROUND OF THE INVENTION

The feasibility of transdermal delivery for a selected drug depends on the efficacious plasma concentration of the drug, the flux of the drug across skin, and the surface area of skin. For reasons of consumer acceptance, the practical surface area of a transdermal system is limited from approximately 5 to 100 $cm^2$. With this limitation on surface area, the therapeutic transdermal administration of many drugs requires an increase in the inherent skin permeability. To this end, a large body of literature has developed concerning compounds which enhance percutaneous absorption.

The ability of water alone to increase skin permeation by hydration or occlusion has been well-documented over the past few decades. While it is published that ethanol can enhance skin permeation in certain instances, even this knowledge is not general in the literature. Two very recent review articles of skin permeation enhancers (B. W. Barry, "Penetration Enhancers in Skin Permeation", *Proceedings of the 13th International Symposium on Controlled Release of Bioactive Materials*, ed. by Chaudry & Thies, Controlled Release Society, Lincolnshire, Ill. 1986 pp 136-137 and Cooper & Berner, "Penetration Enhancers", in *The Transdermal Delivery of Drugs*, Vol. II ed. by Kydonieus and Berner, CRC Press, Boca Raton, Fla. 1986 pp. 57-62) fail to mention ethanol. In current literature, it is stated that ethanol is added in the estradiol transdermal system to solubilize the drug (Int. J. Pharmaceut. 32:159-163, 1986) and that ethanol does not increase the skin permeability to estradiol.

Although the role of ethanol is not generally recognized in the current art, many studies of ethanol and skin have been published. The established maximum skin permeation of ethanol is 400-800 $mcg/cm^2/hr$ (Physiol. Rev. 51:702-747, 1971) and certainly no greater than 1300 $mcg/cm^2/hr$ (U.S. Pat. No. 4,379,454). Ethanol is often included in topical formulations as a volatile excipient which evaporates to deposit the active ingredients on the skin, but does not alter skin permeability.

The use of ethanol to increase skin permeation in an estradiol transdermal system is based on a flux range for ethanol of 100-800 $mcg/cm^2/hr$ and the finding that skin permeation from neat ethanol is as good or better than from aqueous ethanol donor solutions. U.S. Pat. No. 4,379,454 refers to this preferred flux range for ethanol and to a preferred membrane which is permeable to ethanol and estradiol, but not to other compounds in the system reservoir. The use of water from 50-75% at most in this reservoir is suggested to lower the solubility of estradiol, but there is no mention of a change in skin permeation due to the aqueous nature of the formulation. The commercial reduction to practice of this system utilizes a neat ethanol gel in the reservoir and a rate-limiting membrane which is permeable to ethanol in the range of 400 $mcg/cm^2/hr$ and is relatively impermeable to water.

Recent studies of skin permeation of the effect of ethanol and aqueous ethanol on the flux of estradiol through hairless mouse skin, levonorgestrel through rat skin, and salicylic acid through human skin conclude that neat ethanol increases skin permeation better than aqueous ethanol.

The use of ethanol for increasing skin permeation of compounds which are ionized in aqueous solutions (including dipolar ions, i.e. zwitterions) at all practical pH values is not found in the literature.

OBJECTS OF THE INVENTION

One object of the invention is to provide a transdermal device suitable for administering drugs at rates not previously feasible.

Another object of the invention is to provide a means of administering a drug substance which could not previously be administered because the inherent flux across skin was too low.

A third object of the invention is to provide a flux enhancing material which is well tolerated, and a means by which the flux enhancement obtainable therefrom can be realized.

SUMMARY OF THE INVENTION

These and other objects are realized by a typical transdermal device having contained therein water, ethanol, and a drug substance wherein the ethanol and water at the transdermal device-skin interface, have activities in the range of about 0.3 to about 0.9 and 0.4 to about 0.95, respectively.

DETAILED DESCRIPTION OF THE INVENTION

The instant invention transdermal device realizes improved transdermal administration rates by controlling the activities of the ethanol and water components. Just about any of the known transdermal devices can be utilized in the practice of the invention with little variation. The only changes which need be made from the known devices are to (1) regulate the barrier(s) through which the drug, ethanol, and water must pass and/or (2) regulate the ethanol/water concentrations in the transdermal device.

Said dosage form may be fabricated to either: (1) simultaneously co-deliver therapeutic agents and aqueous alcohol from a reservoir, (2) control delivery (by a membrane) of alcohol or water from a reservoir while the drug resides in either a contact adhesive or a separate reservoir, (3) control delivery, by a membrane, of the drug or ethanol or ethanol and water from a single reservoir, or (4) present the therapeutic agent and aqueous ethanol to the skin from a monolithic matrix design.

Surprisingly, it has now been discovered that lower alkanol/water systems at the skin surface result in permeability changes in the skin, which changes are suitable for a large number of drug substances to be administered at a variety of rates, many of which not previously obtainable.

This discovery is of a previously unknown synergism between water and lower alkanols on human skin resulting in mutual flux enhancement. The flux of the alcohol, water, or drug through skin are maximized to an extent significantly greater than previously observed, and as a result, transdermal devices which optimize this synergism by confining the lower alcohol and water activities at the skin-device interface to the range 0.3 to 0.9 and 0.4 to 0.95, respectively, have been invented.

The transdermal device of the invention can be of any type known in the art including the monolithic, matrix, membrane, and other types typically useful for administering drugs by the transdermal route. Such devices are disclosed in U.S. Pat. Nos. 3,996,934; 3,797,494; 3,742,951; 3,598,122; 3,598,123; 3,731,683; 3,734,097; 4,336,243; 4,379,454; 4,460,372; 4,486,193; 4,666,441; 4,615,699; 4,681,584; and 4,558,580 among others; the disclosures of which are incorporated herein by reference. To achieve the advantages of the instant invention, the known devices are modified or limited so that the barriers through which the ethanol, water, and drug must pass allow the substances to pass therethrough at rates which will result in the appropriate water and ethanol activities to be obtained at the transdermal device/skin interface region. Alternatively, or in conjunction therewith, the ethanol and water content of the transdermal device can be modified so as to achieve the above result.

Control of the presentation of both water and alcohol to the skin surface allows the alcohol to permeate the skin at a rate of 2000–4000 mcg/cm$^2$/hr whereas the art teaches that the maximum flux of ethanol through skin is 600–1300 mcg/cm$^2$/hr. The biologically active agent follows the alcohol through the skin, and consequently, the increased alcohol permeation implies increased percutaneous absorption of the drug.

The simplest situation is a transdermal device having a reservoir formed between a drug, ethanol, and water permeable membrane and a drug, ethanol, and water impermeable backing layer, with the drug, water, and ethanol being contained in the reservoir. When the membrane is such that there is no fractionation of the water/lower alkanol, preferably ethanol (i.e. water and the alcohol cross the membrane and are presented at the transdermal device/skin interface in the same ratio as in the reservoir), then the activities of ethanol and water within the transdermal device are the same as those desired to be delivered at the device/skin interfacial region, which is about 0.3 to about 0.9 for the lower alkanol, preferably ethanol and 0.4 to about 0.95 for water, when calculated using neat ethanol and water at 32° C. and atmospheric pressure as the standard state (assuming partial pressure can be treated as ideal gases). Similarly, monolithic and matrix type devices which deliver ethanol and water to the device/skin interfacial region in the same ratio they are found in the device have the same limitations.

The term "activity" shall be defined to have its standard meaning to be found in any standard text book on physical chemistry or thermodynamics. The activity relates the chemical potential of the compound in its selected state to its chemical potential in a standard state. Activity may be considered a generalization of the mole fraction concept to the case of non-ideal systems. In permeation experiments, the driving force for diffusion relates to activity gradients. The choice of standard state must be defined consistently by the experimenter and throughout this invention, the standard states for alkanol and water are respectively, neat alkanol and water at 32° C. and atmospheric pressure. The activities for aqueous alkanol solutions may be interpolated from their partial pressures (International Critical Tables) and it is assumed that the partial pressures may be treated as ideal gases.

Materials suitable for alkanol/water/drug permeable barriers must have a lower alkanol, preferably ethanol, flux of at least 2.5 mg/cm$^2$/hr, preferably at least 3 mg/cm$^2$/hr, most preferably at least 4 mg/cm$^2$/hr, and a water flux of at least 0.9 mg/cm$^2$/hr, preferably at least 2.5 mg/cm$^2$/hr, most preferably at least 3.5 mg/cm$^2$/hr. For convenience purposes, this is measured by placing a portion of membrane or membrane/adhesive laminate in a diffusion cell and filling one side with a 70%, aqueous ethanol. After a period of time the amounts of water and alkanol that have crossed the membrane are determined. Typically, when measuring ethanol flux, the receiver side is water. When measuring water flux, either a) the donor side is $^3$H$_2$O and the receiver side is water or b) the donor side is water and the receiver side is air.

For non-membrane barriers, i.e. monolithic or matrix devices, a 1 mil thick sample is constructed having a 70% aqueous lower alkanol, preferably ethanol solution contained therein. Alkanol and water fluxes are measured as the amount of those substances migrating from the device to a receiving portion, which portion is water for alkanol measurement and air for the flux measurement of water.

If the membrane or other barrier does not have a sufficiently high flux, the thickness of the membrane or barrier can be reduced. The only limitations on thinning this membrane or barrier are a) the possibility of a reduction of quality control because thinner membranes are more prone to tear and less reproducible and b) loss of extended use from the application of a single device, since a thinner matrix or monolith limits the amount of drug or drug formulation that can be contained in the device.

In addition, the second factor that must be taken into account is the activity of the lower alkanol and the water. For calculation purposes, one utilizes neat alkanol and/or water at 32° C., and atmospheric pressure as the standard state and partial pressures are assumed to be treated as in an ideal gas. Under these conditions, the activity of ethanol in the device, particularly in the drug depot region is from about 0.3 to about 0.9 while the activity of water is from about 0.4 to about no greater than 0.95.

Typically preferred membrane barrier materials include ethylene vinyl acetate having at least 20% vinyl acetate, ethylene/vinyl alcohol, polyurethane, microporous membranes of polypropylene, polyethylene, nylon, polycarbonate, and many others, as well as blends thereof.

Monolithic and matrix type barrier components are preferably of:

(1) Porous polymers or open-cell foam polymers, such as PVC, polyurethanes, polypropylenes, etc.

(2) Highly swollen or plasticized polymers such as cellulose, HEMA or MEMA or their copolymers, HPMC, HEMC, etc., PV alcohol/ PVP, or other hydrogels, or PVC, polyurethane, ethylene vinyl acetate, or their copolymers.

(3) Gels of liquids containing aqueous ethanol, where gels can be prepared with gelling agents such as PVP, CMC, Klucel, HPMC, alginates, kaolinate, bentonite, or montmorillonite, other clay fillers, stearates, silicon dioxide particles, etc.

(4) Nonwoven materials made of textiles, celluloses, polyurethanes, polyester or other fiber.

(5) Sponges such as natural or foamed polymers such as PVC.

(6) Adhesives such as the known dermatologically acceptable pressure sensitive adhesives, inclusive of silicone adhesives.

Exemplary adhesives include polyurethanes; acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tertbutylacrylamide, itaconic acid, vinylacetate, N-branched alkyl maleamic acids wherein the alkyl group has 10 to 24 carbon atoms, glycol diacrylates, or mixtures of these; natural or synthetic rubbers such as styrenebutadiene, butylether, neoprene, polyisobutylene, polybutadiene, and polyisoprene; polyvinylacetate; unreaformaldehyde resins; phenolformaldehyde resins; resorcinol formaldehyde resins, cellulose derivatives such as ethyl cellulose, methyl cellulose, nitrocellulose, cellulose acetatebutyrate, and carboxymethyl cellulose; and natural gums such as guar, acacia, pectins, starch, dextrin, albumin, gelatin, casein, etc. The adhesives may be compounded with tackifiers and stabilizers as is well known in the art.

Exemplary silicone adhesives include: silicone elastomers based on monomers of silanes, halosilanes, or $C_1$–$C_{18}$ alkoxysilanes, especially polydimethylsiloxanes which may be used alone or formulated with a silicone tackifier or silicone plasticizer which are selected from medically acceptable silicone fluids, i.e. non-elastomeric silicones based on silanes, halosilanes or $C_1$–$C_{18}$ alkoxysilanes. Typical silicone adhesives are available from Dow Corning under the tradename SILASTIC.

For those adhesives which are impermeable to one or more of the water, ethanol, or drug, the adhesive is placed on an area through which such materials would not be otherwise passing, i.e. the periphery of the delivery area, or are present in a discontinuous pattern so as not to overly limit the flow of the components.

Without limiting the invention, the aforementioned polymeric barrier materials may be selected from Polycarbonates, i.e. linear polyesters or carbonic acids in which carbonate groups recur in the polymer chain, by phosgenation of a dihydroxy aromatic such as bisphenol A. Such materials are sold under the trade designation Lexan by the General Electric Company.

Polyvinylchlorides; one such material is sold under the trade designation Geon 121 by B. G. Goodrich Chemical Company.

Polyamides such as polyhexamethylene adipamide and other such polyamides popularly known as "nylon". One particularly advantageous material is that sold under the trade name "NOMEX" by E. I. DuPont de Nemours & Co.

Modacrylic copolymers, such as that sold under the trade designation DYNEL, are formed of polyvinylchloride (60 percent) and acrylonitrile (40 percent), styrene-acrylic acid copolymers, and the like.

Polysulfones such as those of the type characterized by diphenylene sulfone groups in the linear chain thereof are useful. Such materials are available from Union Carbide Corporation under the trade designation P-1700.

Halogenated polymers such as polyvinylidene fluoride sold under the trade designation Kynar by Pennsalt Chemical Corporation, polyvinylfluoride sold under the trade name Tedlar by E. I. DuPont de Nemours & Co., and the polyfluorohalocarbon sold under the trade name Aclar by Allied Chemical Corporation.

Polychlorethers such as that sold under the trade name Penton by Hercules Incorporated, and other such thermoplastic polyethers.

Acetal polymers such as the polyformaldehyde sold under the trade name Delrin by E. I. DuPont de Nemours & Co., and the like.

Acrylic resins such as polyacrylonitrile polymethyl methacrylate, poly n-butyl methacrylate and the like.

Other polymers such as polyurethanes, polyimides, polybenzimidazoles, polyvinyl acetate, aromatic and aliphatic, polyethers, cellulose esters, e.g., cellulose triacetate; cellulose; colledion (cellulose nitrate with 11% nitrogen); epoxy resins; olefins, e.g., polyethylene, polypropylene; polyvinylidene chloride; porous rubber; cross linked poly(ethylene oxide); cross-linked polyvinylpyrrolidone; cross-linked poly(vinyl alcohol); polyelectrolyte structures formed of two ionically associated polymers of the type as set forth in U.S. Pat. Nos. 3,549,016 and 3,546,141; derivatives of polystyrene such as poly(sodium styrenesulfonate) and poly(vinylbenzyltrimethyl-ammonium chloride); poly(hydroxyethylmethacrylate); poly(isobutylvinyl ether), and the like, may also be utilized. A large number of copolymers which can be formed by reacting various proportions of monomers from the aforesaid said list of polymers are also useful.

The back flux of water through the skin, i.e., the transepidermal water loss, must often be included as a factor in determining the presentation of alcohol and water to the skin surface. If an aqueous solution obtains on the skin surface, then the composition of that aqueous ethanol solution should be between 35% and 90% (v/v) ethanol without adjustment for the drug or other excipients and more preferably between 45% and 85% (v/v) ethanol without adjustment for the drug or other excipients. Typically, the aqueous ethanol solution has a fixed chemical activity of the drug or is a saturated solution of the drug. Preferably, the chemical activities (as calculated from their partial pressures interpolated to 32° C. and the assumption of the ideal gas law) of ethanol and water at the skin surface should be greater than 0.5 and 0.35, respectively and both should be less than 0.9. The activity criteria is valid for (1) both transdermal systems with membranes for which the reservoir composition and the skin, membrane, and adhesive permeabilities to ethanol, water, and drug are accounted for and (2) monolithic matrix systems.

When the biologically active agent is a lipophilic liquid or low-melting compound, the active ingredient or ingredients may further alter the flux of ethanol. That is the drug, alcohol, and water may all mutually enhance the others skin permeation. Under such conditions, the optimal enhancement is obtained by presenting to the skin surface a saturated drug solution of aqueous alcohol which is already optimized by the previously mentioned criteria.

When the biologically active agent is ionizable, the pH at the skin surface may be selected so that the solubility of the drug is maximal in the aqueous alkanol solutions; nonetheless the pH is preferably between 3.5 and 9.5. Such transdermal systems may be (1) monolithic matrix devices containing a salt of the drug or buffering agent in the aqueous ethanol or (2) membrane devices which contain either a salt of the drug or a buffering agent either located in the aqueous ethanol solution or in the adhesive. Other variants will be apparent to those of ordinary skill.

MODES FOR CARRYING OUT THE INVENTION

Figure 1:
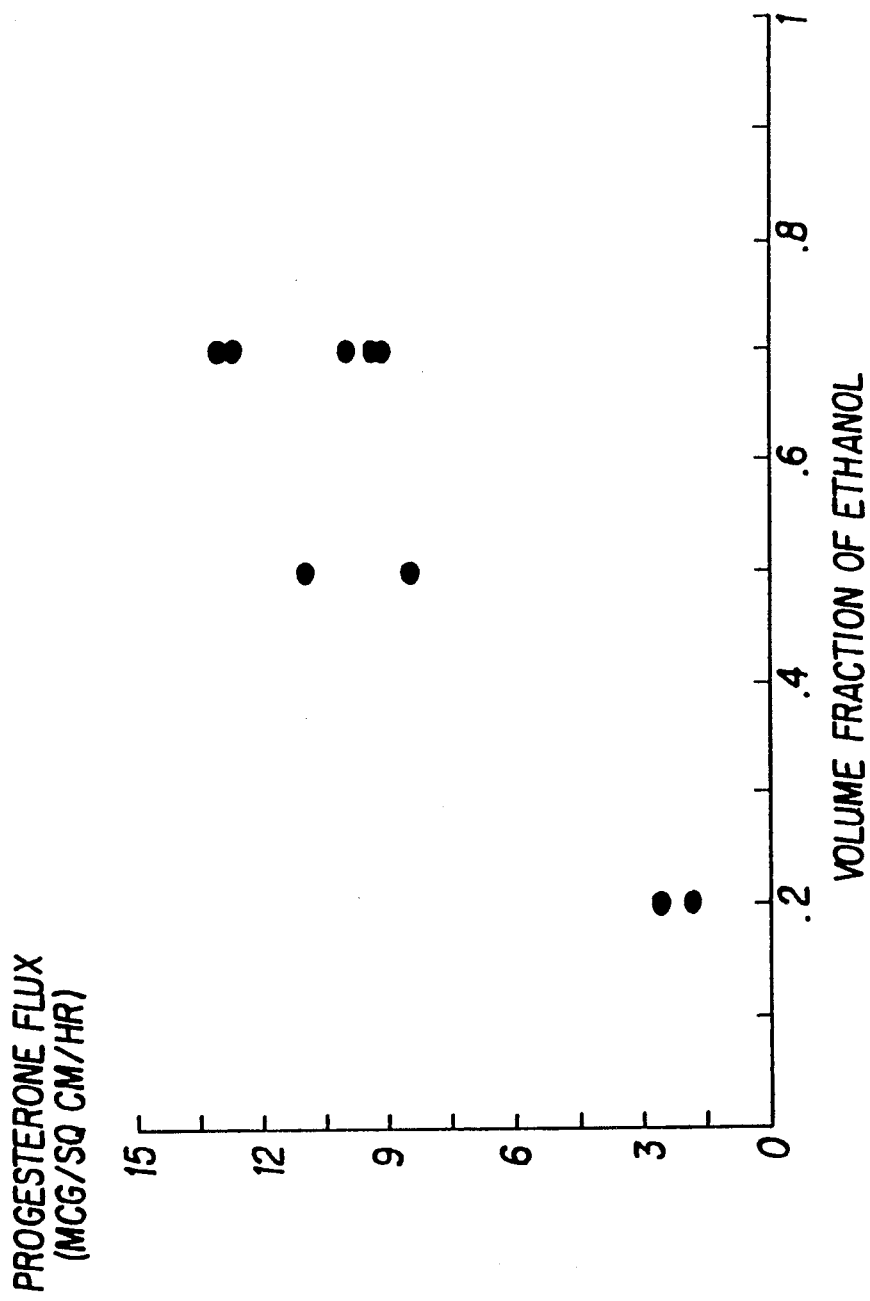
FIG. 1 is a graph of the steady-state flux across the epidermis of progesterone, a lipophilic drug, versus the volume fraction of ethanol in the donor solution not accounting for the concentration of drug. Note the large increase in the flux from the optimized aqueous ethanol reservoir compared to both neat water and neat ethanol.

In the art of transdermal drug delivery, there are two basic designs for carrying out delivery: (1) a membrane device and (2) a monolithic matrix device. The membrane device typically has four layers: (1) an impermeable backing, (2) a reservoir layer, (3) a membrane layer which may be a dense polymer membrane or a microporous membrane, and (4) a contact adhesive layer which either covers the entire device surface in a continuous or discontinuous coating or surrounds the membrane layer. Examples of materials that may be used to act as an impermeable layer are high, medium, and low density polyethylene, polypropylene, polyvinylchloride, polyvinylidene chloride, polycarbonate, polyethylene terephthalate, and polymers laminated or coated with aluminum foil. Others are disclosed in the standard transdermal device patents mentioned earlier. In embodiments of the invention in which the reservoir layer is fluid or, if desired, when the reservoir is a polymer, the outer edge of the backing layer may overlay the edge of the reservoir layer and be sealed by adhesion or fusion to the diffusion membrane layer. In such instances, the reservoir layer need not have exposed surfaces.

The reservoir layer is underneath the impermeable backing and contains ethanol, typically water, and may or may not contain the drug. The amount of drug in the reservoir depends on the desired rate of absorption through the skin from the device and the intended duration of therapy. The amount of ethanol is typically from 35% to 95% by volume with only the ethanol and water content included. However, the ethanol content may exceed 95% for membrane and adhesive laminates which are highly permeable to ethanol, but highly impermeable to water. The ethanol:water content of the reservoir may be designed to give (1) a concentration of ethanol:water on the skin surface between 0.25, preferably 0.35, more preferably 0.45, and 0.9 volume fraction and preferably in the range 0.45 to 0.85 volume fraction or (2) chemical activities of ethanol and water on the skin surface (as calculated from the interpolated partial pressures to 32° C. and the ideal gas law assumption) greater than 0.3, preferably 0.5, and 0.4, preferably 0.5, respectively and both should be less than 0.9 or (3) a flux of ethanol through skin of greater than 900 mcg/cm$^2$/hr while at least 50% of the diffusional resistance is provided by the membrane and adhesive laminate or (4) a flux of ethanol through skin greater than 1500 mcg/cm$^2$/hr and a flux from the applied transdermal system to the skin of at least 1500 mcg/cm$^2$/hr. The reservoir layer may include diluents, stabilizers, vehicles, gelling agents, and the like in addition to ethanol, water and drug. Known gelling agents such as carboxy polymethylene, ethylene maleic anhydride, hydroxyethyl cellulose, polyacrylamide, ethylhydroxyethyl cellulose, hydroxypropyl cellulose, and poly (methyl vinyl ether maleic anhydride) may be included to make a gel.

The diffusion membrane layer of the laminate device may be made of a dense or microporous polymer film that has the requisite permeability to the drug, ethanol, and water. In the preferred system design, the membrane controls the rates of presentation of ethanol and water to the skin, but the rate of permeation of drug through the skin is only controlled through the ethanol and water rates of presentation. Preferably the membrane is impermeable to ingredients other than the drug, ethanol and water in the reservoir layer, although when buffering at the skin surface is desired, the membrane should be permeable to the buffer in the formulation as well. Examples of polymer film that may be used to make the membrane layer are disclosed in U.S. Pat. Nos. 3,797,454 and 4,031,894. The preferred materials are polyurethane, ethylene/vinyl alcohol copolymers or ethylene/vinyl acetate of a content greater than 20% vinyl acetate, preferably greater than 25% vinyl acetate, more preferably at least 28% vinyl acetate, and most preferably greater than 34% vinyl acetate.

The contact adhesive layer is the means to affix the device to the skin. During the time between manufacture and use of the transdermal system, either drug or ethanol-water may be absorbed into the adhesive layer. In a second preferred design of the transdermal device, the supply of drug resides in the adhesive and the membrane is impermeable to the drug, but still controls the rate of presentation of ethanol and water to the skin.

The second class of transdermal systems is represented by monolithic matrices. Examples of such monolithic devices are U.S. Pat. Nos. 4,291,014, 4,297,995, 4,390,520, and 4,340,043. Others are known to those of ordinary skill in this art. Any incorporation of the present invention in a monolithic matrix must contain ethanol and water in a manner that either yields (1) a concentration of ethanol in aqueous ethanol on the skin surface between 0.25, preferably 0.35, and 0.9 volume fraction and preferably in the range 0.45 to 0.85 (not including drug, polymer, or excipient content) or (2) chemical activities of lower alkanol, preferably ethanol, and water on the skin surface, as calculated from the interpolated partial pressures to 32° C. and the ideal gas law assumption, greater than 0.3, preferably 0.5, and 0.4, preferably 0.5, respectively and both should be less than 0.9, or (3) a flux of ethanol through skin greater than 1500, preferably at least 1750, more preferably at least 2000 mcg/cm$^2$/hr.

The modes of the present invention may be formulated to incorporate pharmaceutically-acceptable or pharmaceutically active agents which are useful in providing activity to the following: (1) the general system or distal sites to produce systemic effects, (2) sites in the stratum corneum, viable epidermis or dermis, or (3) sites in any of the glands or structures in and beneath the dermis. Examples of such pharmaceutically active agents may be found in U.S. Pat. Nos. 3,989,816, 4,343,798, or 4,199,475 or in standard texts such as Goodman et al. The *Pharmacological Basis of Therapeutics*, 7th Ed., *Remington's Pharmaceutical Sciences*, *Burger's Medicinal Chemistry*, or *Martindalt The Extra Pharmacopaeia*.

While virtually any drug can be administered transdermally with the present system, it is especially useful to administer a drug selected from: antitubercular agents, such as isoniazid and rifampin; analgesics such as nicomorphine, buprenorphine, fentanyl and sufentanyl; muscle relaxants, such as baclofen; β-adrenergic receptor agonists and antiasthmatics, such as theophylline, formoterol, albuterol and terbutaline; steroids, such as estradiol, progesterone, norethindrone, norethisterone acetate, prednisone, prednisolone, methyltestosterone, and desoxycorticosterone; anticholinergics, such as scopolamine and methscopolamine; vasodilators, such as nitroglycerin; antihypertensives, such as metoprolol; antihistamines, such as triprolidine, tripelenamine, and diphenhydramine; cholinergic agents, such as arecoline; CNS stimulants, such as methylphenidate and nikethimide; angiotensin converting enzyme inhibitors, such as enalapril, 1-carboxymethyl-3-[1-carboxy-3-phenyl-(1S)-propylamino]-2,3,4,5-tetrahydro-1H(3S) [1]benzazepine-2-one, 3-[(5-amino-1-carboxy-1S-pentyl)aminl-2,3,4,5-tetrahydro-2-oxo-3S-1H-1-benzazepine-1-acetic acid or 3-([1-ethoxycarbonyl-3-phenyl-(1S)-propyl]amino)2,3,4,5-tetrahydro-2-oxo-(3S)-benzazepine-1-acetic acid monohydrochloride; nicotine, physotigmine, and naloxone; CNS agents such as bromocriptine, (±)-trans-1,3,4,4a,5,10b-hexahydro-4-propyl-2H-[1]benzopyrano[3,4-b]pyridine-9-ol mono-hydrochloride, (±)-trans-1,3,4,4a,5,10b-hexahydro4-propyl-2H-[1]benzopyrano[3,4-b]pyridin-7-ol monohydrochloride and serotoninergic agonist and antagonists; and others as will be apparent to those of ordinary skill. The only limitation to use of this system for a drug for transdermal use is that the drug have at least one form which permeates through the skin and any barriers of the system between the drug and the skin. If a topical drug is being administered, the only restriction is that there be at least one form of the drug which can migrate through the system barriers between the drug and the skin.

A preferred class of drugs for use in the system of the invention is: buprenorphine, fentanyl, sufentanyl, terbutaline, formoterol, albuterol, theophyline, estradiol, progesterone, scopolamine, enalapril, 1-carboxymethyl3-[1-carboxy-3-phenyl-(1S)-propylamino]-2,3,4,5-tetrahydro- 1H-(3S) [1]benzazepine-2-one, 3-[(5-amino-1carboxy-1S-pentyl) amino-2,3,4,5-tetrahydro-2-oxo-3S-1H-1-benzazepine-1-acetic acid, 3-([1-ethoxycarbonyl-3-phenyl-(1S)-propyl]amino)-2,3,4,5-tetrahydro-2-oxo-(3S)-benzazepine-1-acetic acid monohydrochloride; nitroglycerin, triprolidine, tripelenamine, diphenhydramine, physostigmine, arecoline, and nicotine.

The invention will be further understood in connection with the following Examples which do not limit but only exemplify, the invention.

EXAMPLE 1

Figure 2:
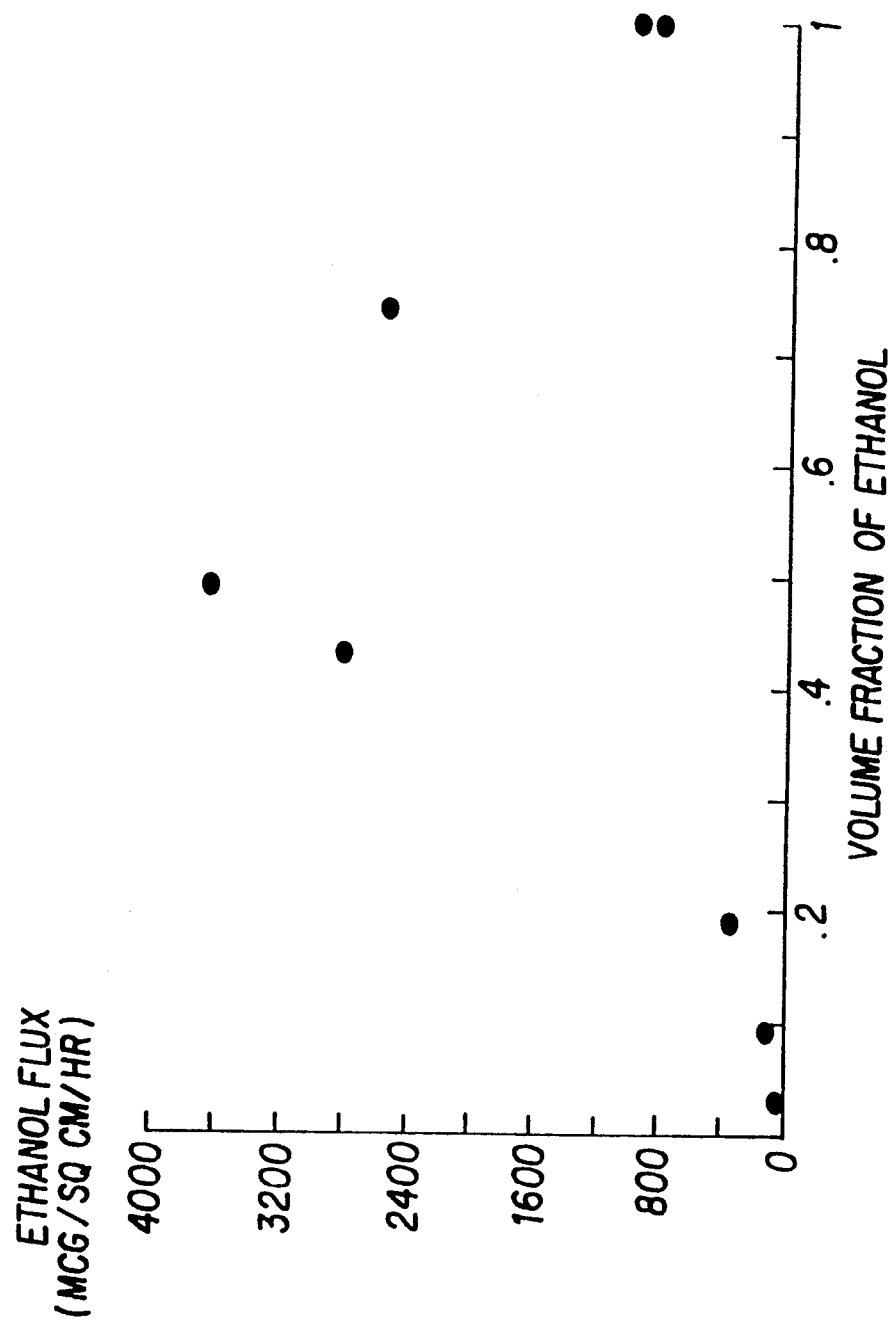
FIG. 2 is a graph of the steady-state flux of ethanol across human epidermis versus the volume fraction of ethanol in the donor solution. Note the optimum in the flux.
Figure 3:
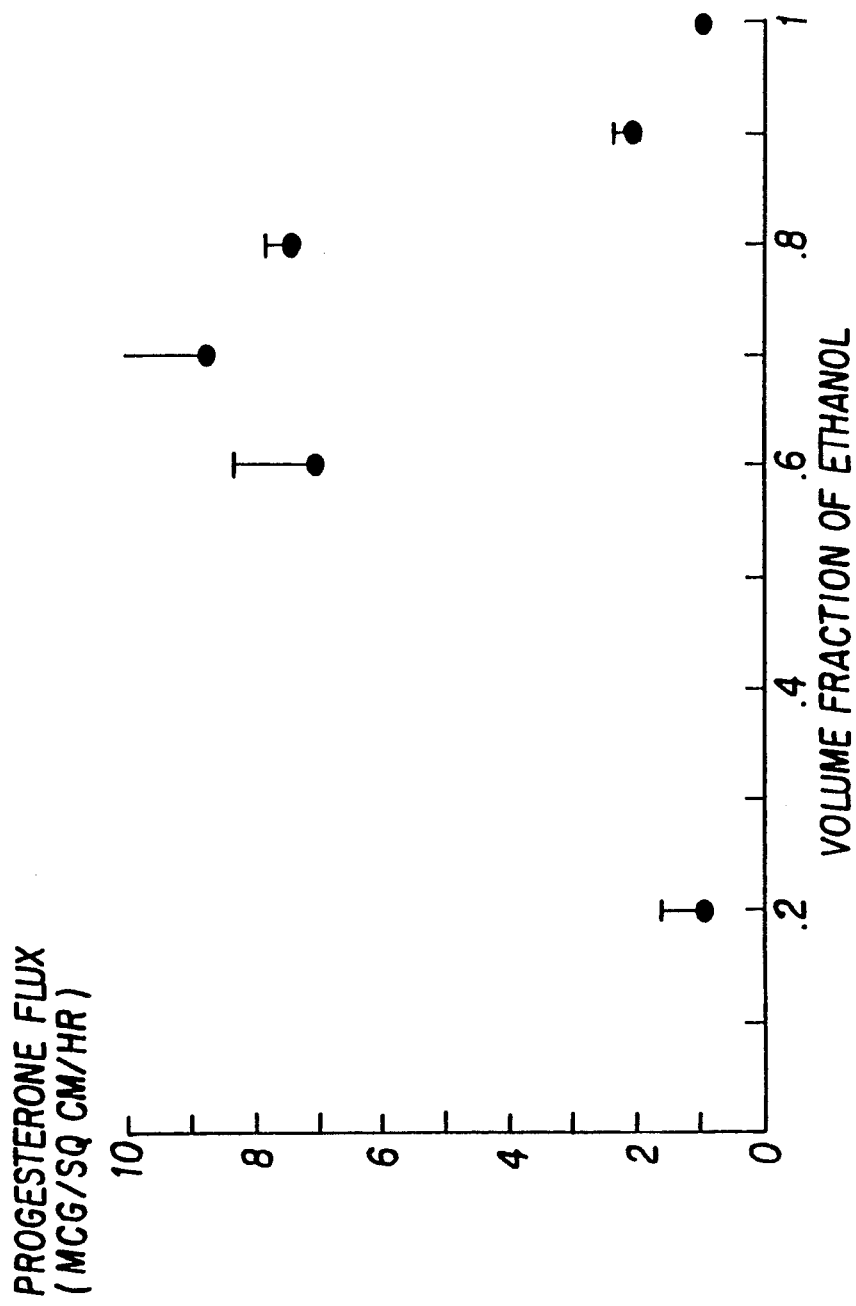
FIG. 3 is a graph of the flux of progesterone across a membrane and adhesive on human epidermis versus volume fraction of ethanol in the aqueous ethanol reservoir.

This Example is based on FIGS. 1–3. The transdermal system has an active drug releasing surface of 10 cm$^2$ and has a polyester backing, a 1 mil polyurethane membrane and a silicone adhesive. The reservoir contains 1.7 ml of ethanol, 0.3 ml water, 200 mg of progesterone as the drug, and 2% Klucel as a gelling agent. As shown in FIGS. 1 and 2, the fluxes of progesterone and ethanol through skin are optimized in the range from 0.4–0.85 volume fraction of ethanol not including the drug or gelling agent. Neat ethanol does not enhance skin permeation nearly as well as this aqueous ethanol reservoir. FIG. 3 shows that with the above mentioned membrane and adhesive the skin permeation exhibits an optimum near 0.7 volume fraction of ethanol. A volume fraction of 0.85 is chosen to allow for the back flux of water and depletion of ethanol during the use of the system.

EXAMPLE 2

A polyurethane sponge containing the ethanol, water, and drug composition of Example 1. An impermeable backing of polyester with a peripheral adhesive is attached to the sponge.

EXAMPLE 3

A polymeric matrix such as a polytetramethylene glycol/HEMA copolymer hydrogel loaded with 0.7 volume fraction of ethanol in aqueous ethanol and the drug. An impermeable polymer foil laminate backs this system and is attached to a peripheral adhesive for applying the system to skin.

EXAMPLE 4

Figure 4:
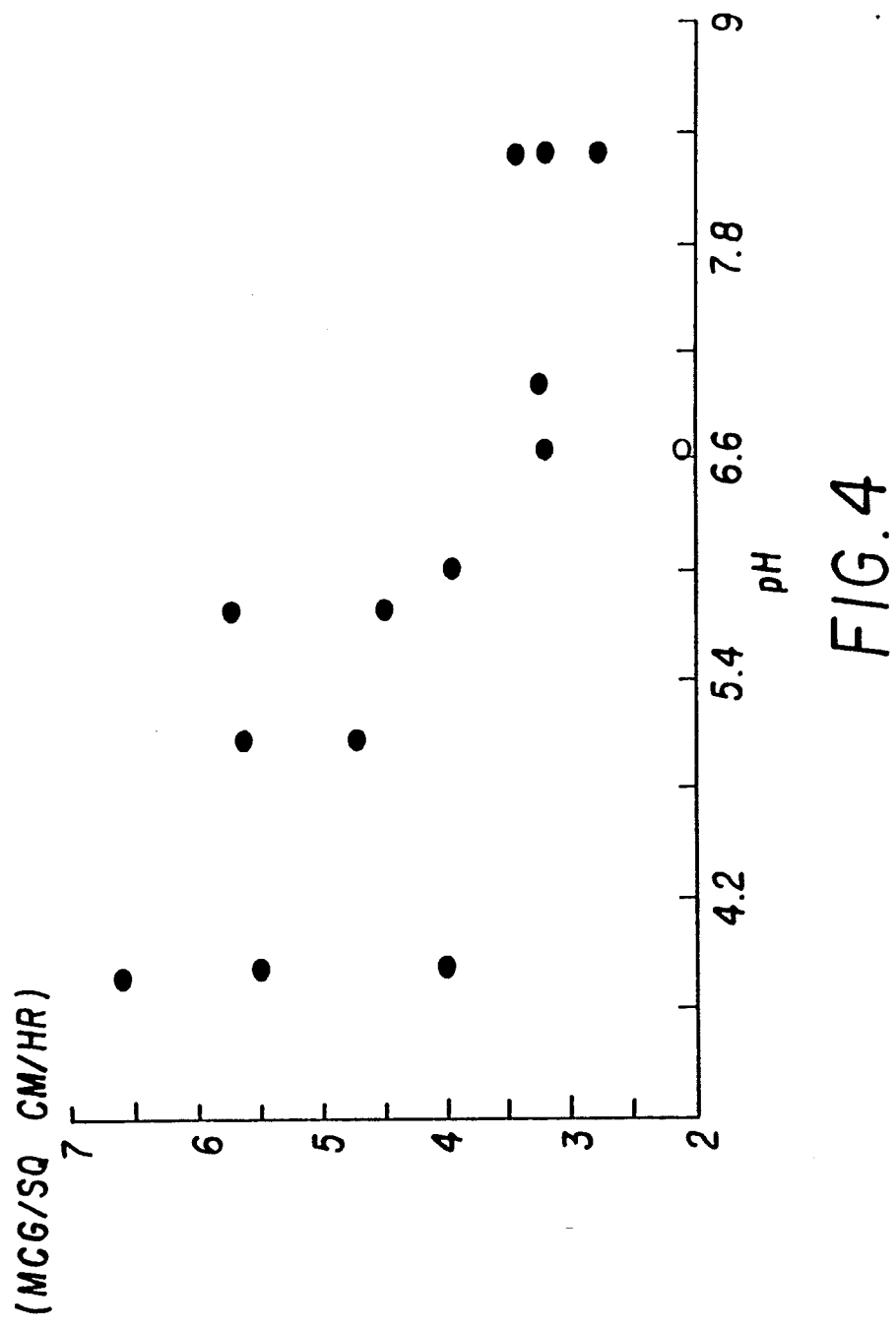
FIG. 4 is a graph of the flux of (±) trans-1,3,4,4a,5,10b-hexahydro-4-propyl-2H-[1]benzopyrano[3,4-b]pyridin-9-ol monohydrochloride, an ionizable drug which is a dopamine autoreceptor agonist, across human epidermis from ethanol: water (7:3) versus pH of that aqueous ethanol solution. In aqueous solutions, the drug is negatively charged below pH 6.5.

This Example is based on FIG. 4 in which the dopamine autoreceptor agonist, (±)trans-1,3,4,4a,5,10b-hexahydro4-propyl-2H-[1]benzopyrano[3,4-b]pyridin-9-ol, an ionizable drug, permeates skin. For this drug the optimal pH of an ethanol:water donor which is 0.7 volume fraction of ethanol is in the range of 4. A microporous membrane such as a microporous polypropylene and a silicone adhesive may be used. The active agent is present at saturation.

EXAMPLE 5

The same active agent as in Example 4 is loaded as a salt, in particular the hydrochloride salt, into the silicone adhesive. A polyurethane membrane and a polyester surround an aqueous ethanol reservoir (0.85 volume fraction of ethanol) containing 2% Klucel as a gelling agent. The salt establishes the low pH at the skin surface.

EXAMPLE 6 AND 7

Figure 5:
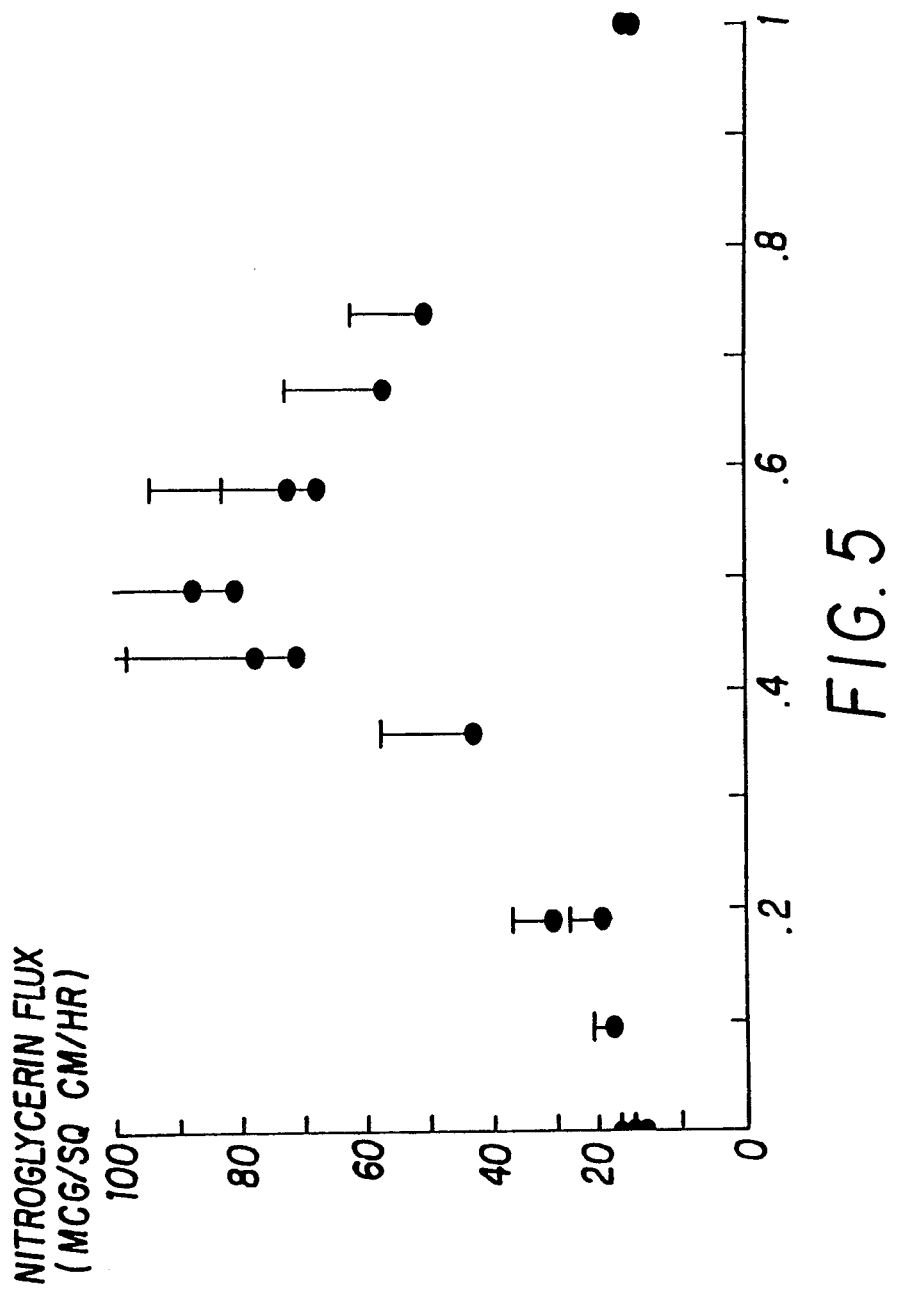
FIG. 5 is a graph of the flux of nitroglycerin across epidermis versus the volume fraction of ethanol in the aqueous ethanol reservoir.
Figure 6:
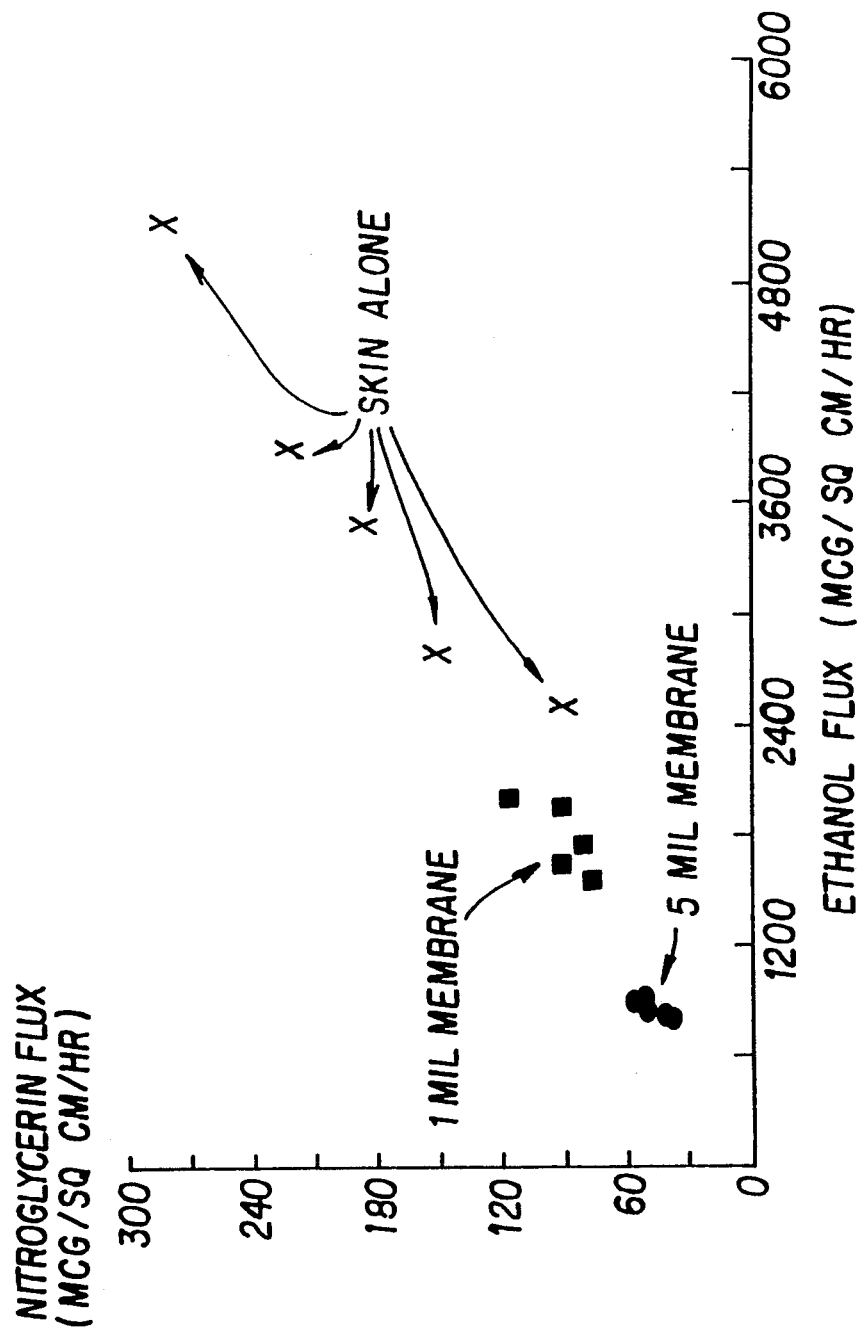
FIG. 6 is a graph of the flux of nitroglycerin versus the flux of ethanol for two different membrane thicknesses and epidermis as compared to epidermis alone.

These Examples are based on FIGS. 5 and 6. A 0.65 volume fraction of ethanol is used in the reservoir. The systems have a 10 cm$^2$ surface area, and use a polyester impermeable backing, a polyurethane membrane, and a silicone adhesive. Two systems with different delivery rates require fill volumes of 0.52 and 1.04 ml of aqueous ethanol, 350 and 700 mg of 10% nitroglycerin on lactose, 1 mil and 5 mil polyurethane membranes, and deliver 0.8 and 1.5 mg/cm$^2$/hr of ethanol, respectively. The increase in nitroglycerin flux is shown in FIG. 5.

Above a volume fraction of 0.8 ethanol, a safety hazard or transportation law infraction may be incurred with nitroglycerin unless the nitroglycerin is kept below 10%. In FIG. 6, the linearity of the fluxes of nitroglycerin versus ethanol through skin and the control membrane adhesive laminates are shown. The nitroglycerin follows the ethanol through skin; the ethanol permeation has been further enhanced by the water and nitroglycerin. Note the added system control of nitroglycerin flux with increasing membrane thickness.

EXAMPLE 8

The transdermal system has an active drug releasing surface of 10 cm$^2$ and has a polyester backing, a 1 mil ethylene/vinyl acetate membrane of vinyl acetate content greater than 20%, a reservoir consisting of ethanol:water (7:3) and saturated with nitroglycerin on lactose. As shown in Table 1, the ethanol and tritiated water permeation increase with vinyl acetate content until the reservoir composition of ethanol and water is delivered to the skin surface. For all of these systems, the skin controls the rate of nitroglycerin permeation. It should be noted that systems with membranes of less than 20% vinyl acetate content are systems previously disclosed in the literature and do not have ethanol or water fluxes which are in the range disclosed by this invention. In contrast, systems with ethylene/vinyl acetate membranes having greater than 20% vinyl acetate content do fall within the range covered by this invention disclosure. Furthermore, as shown in Table 2, the fluxes of nitroglycerin through skin from those systems with membranes of higher vinyl acetate content are as much as a factor of 2 better than the best of the systems previously disclosed in the literature.

TABLE 1

Fluxes Through Ethylene Vinyl Acetate Membranes

| Vinyl Acetate Content (%) | Ethanol (mg/hr) | $^3$H$_2$O (mg/hr) | Nitroglycerin (mg/hr) |
|---|---|---|---|
| 9 | 9 ± 2 | 0.5 | 2.4 ± 0.3 |
| 18 | 19 ± 1 | 4 ± 0.3 | 5 ± 0.7 |
| 28 | 57 ± 6 | 17 ± 3 | 10 ± 0.5 |
| 40 | 150 ± 4 | 63 ± 9 | 21 ± 0.3 |

TABLE 2

Fluxes of Nitroglycerin Through Skin and Ethylene Vinyl Acetate Membranes of Differing Vinyl Acetate Contents

| Vinyl Acetate Content (%) | Flux of Nitroglycerin (mcg/cm$^2$/hr) |
|---|---|
| 9 | 30 |
| 18 | 60 |
| 28 | 66 |
| 40 | 120 |

EXAMPLE 9

A transdermal system consisting of a reservoir composition containing 10% nitroglycerin (w/v) in ethanol:water (85:15 v/v) and 2% hydroxy propyl methyl cellulose as a gelling agent, an ethylene/vinyl acetate membrane of vinyl acetate content greater than 20% and a silicone adhesive used either a) on the periphery, but not the drug-permeating area (face) of the device or b) pattern-printed on the face or c) on the face in a porous or foamed fashion or d) on the face containing filling materials that will dissolve or swell in the presence of ethanol or water or e) a silicone adhesive less than or equal to 1 mil in thickness on the face of the device. In current-marketed transdermal devices, the adhesive is typically between 1.5 and 3 mils thick and is on the face of the device. In Table 3, the fluxes of ethanol and nitroglycerin through skin are compared for the above reservoir with a 32.8% vinyl acetate contents membrane (prepared by blending two resins) with a peripheral adhesive (membrane alone) versus a 2 mil silicone face adhesive (membrane plus adhesive). The use of a conventional silicone adhesive layer alters the water activity at the skin surface so that it does not fall within the range of this invention disclosure. That is, the tritiated water flux through the combined membrane adhesive laminate is smaller than the range disclosed by this invention while the ethanol flux is within the range disclosed by this invention. In this example, optimization of both the adhesive and membrane layers as taught by this invention improves the nitroglycerin flux by more than a factor of two.

TABLE 3

Fluxes of Nitroglycerin and Ethanol Through a 32.8% Vinyl Acetate Content Membrane Plus Skin With and Without Silicone Face Adhesive From an Ethanol:Water Reservoir (85:15)

| | Nitroglycerin Flux (mcg/cm$^2$/hr) | Ethanol Flux (mcg/cm$^2$/hr) |
|---|---|---|
| Skin alone without ethanol in donor | 15 ± 7 | — |
| Skin alone from ethanol:water (70:30) | 85 ± 15 | 3200 ± 600 |
| Membrane alone and Skin | 82 ± 26 | 3200 ± 500 |
| Membrane and Adhesive and Skin | 37 ± 10 | 1410 ± 240 |

What is claimed is:

1. A transdermal drug delivery system comprising
   (i) an occlusive, impermeable polymeric backing layer;
   (ii) a drug depot on one side thereof;
   (iii) a removable, occlusive covering layer over said drug depot; and
   (iv) an adhesive means by which said delivery system, absent said removable covering layer may be affixed to an intended patient; said drug depot containing a drug formulation comprising a transdermally administrable pharmaceutically acceptable pharmaceutically active agent or a precursor thereof, water and ethanol said active agent or precursor thereof being present in a pharmaceutically effective amount; said ethanol and said water being present in a volume:volume ratio of from 30:70 up to less than 95:5 such that said ethanol, water and drug are delivered to a patient's skin, which patient has applied said system absent said removable covering layer to said patient's skin, in amounts that said drug is delivered in a transdermally administrable efficacious amount, said water has an activity at said patients skin of about 0.4 to about 0.95 and said ethanol, at said patient's skin, has an activity of 0.3 to about 0.9, and wherein, once applied to said patient's skin, said ethanol has a flux from said system to said skin of at least 1500 mcg/cm$^2$/hr and through said skin of at least 1500 mcg/cm$^2$/hr.

2. The system of claim 1 wherein said composition further comprises at least one further transdermal drug delivery device acceptable adjuvant.

3. The system of claim 1 wherein said volume:volume ratio is from 45:55 up to and including 85:15.

4. The system of claim 5 wherein said volume:volume ratio is from 65:35 up to and including 75:25.

5. The system of claim 1 wherein said water and ethanol are delivered to said patient's skin so as to result in an ethanol activity of at least 0.5.

6. The system of claim 1 wherein, once applied to a patient's skin, said alkanol ethanol has a potential flux through said skin of at least 1500 mcg/cm$^2$/hr, and an actual flux from said system through said skin of at least 900 mcg/cm$^2$/hr, and at least 50% of the diffusional resistance is provided by said system.

7. A dosage form for transdermally administering a pharmaceutically active agent which dosage form comprises
 a) an impermeable backing,
 b) a rate-controlling membrane of polyurethane or ethylene/vinylacetate of greater than 20% vinyl acetate and from 0.5 to 10.0 mils thick,
 c) a silicone-based or acrylic-based pressure-sensitive adhesive on said rate controlling membrane distal from said backing,
 d) a reservoir formed by a and b,
 e) an aqueous pharmaceutically acceptable lower alkanol reservoir composition having a volume fraction of said ethanol of from 0.35 to 0.9 calculated based on said ethanol alkanol and water only, and
 f) said pharmaceutically active agent.

8. The dosage form of claim 7 further comprising a salt of said pharmaceutically active agent or a buffering agent in said adhesive.

9. A dosage form of claim 7 wherein the membrane is microporous and the adhesive is pressure-sensitive.

10. A dosage form of claim 7 where the membrane allows said ethanol to permeate therethrough between 1.5 and 12 mg/cm$^2$/hr and water to permeate therethrough at between 0.5–10 mg/cm$^2$/hr and the adhesive is pressure-sensitive.

11. A unit dosage form according to claim 7 wherein said membrane is impermeable to said pharmaceutically active agent and said adhesive contains said pharmaceutically active agent.

* * * * *

UNITED STATES PATENT AND TRADEMARK OFFICE
CERTIFICATE OF CORRECTION

PATENT NO. : 5,064,654

DATED : November 12, 1991

INVENTOR(S) : BRET BERNER, CHARLES EBERT, GERARD C. MAZZENGA, JOHN H. OTTE

It is certified that error appears in the above-identified patent and that said Letters Patent is hereby corrected as shown below:

Column 13:

Claim 4, line 1, change "claim 5" to --claim 1--

Claim 7, lines 12-13, change "lower alkanol to --ethanol--

Claim 7, line 15, delete "alkanol"

Signed and Sealed this

Eleventh Day of January, 1994

Attest:

BRUCE LEHMAN

Attesting Officer

Commissioner of Patents and Trademarks